US010210409B1

United States Patent
Migneco et al.

(10) Patent No.: US 10,210,409 B1
(45) Date of Patent: Feb. 19, 2019

(54) SEATING SYSTEM WITH OCCUPANT STIMULATION AND SENSING

(71) Applicant: Lear Corporation, Southfield, MI (US)

(72) Inventors: Francesco Migneco, Salene, MI (US); David Gallagher, Sterling Heights, MI (US); Arjun Yetukuri, Rochester Hills, MI (US)

(73) Assignee: Lear Corporation, Southfield, MI (US)

( * ) Notice: Subject to any disclaimer, the term of this patent is extended or adjusted under 35 U.S.C. 154(b) by 0 days.

(21) Appl. No.: 15/890,996

(22) Filed: Feb. 7, 2018

(51) Int. Cl.
| | |
|---|---|
| *B60N 2/00* | (2006.01) |
| *A61B 5/18* | (2006.01) |
| *G06K 9/00* | (2006.01) |
| *B60K 28/06* | (2006.01) |
| *G08B 21/06* | (2006.01) |
| *B60W 50/14* | (2012.01) |

(52) U.S. Cl.
CPC ............ *G06K 9/00845* (2013.01); *A61B 5/18* (2013.01); *B60K 28/066* (2013.01); *B60N 2/002* (2013.01); *G06K 9/00838* (2013.01); *G08B 21/06* (2013.01); *B60W 2050/143* (2013.01)

(58) Field of Classification Search
CPC .... B60N 2/44; B60N 2002/4485; B60N 2/90; G08B 6/00; B60Q 9/00; A61B 5/005; A61B 5/18
See application file for complete search history.

(56) References Cited

U.S. PATENT DOCUMENTS

| | | | |
|---|---|---|---|
| 8,903,494 B2 | 12/2014 | Goldwasser et al. | |
| 9,002,458 B2 | 4/2015 | Pal et al. | |
| 9,014,811 B2 | 4/2015 | Pal et al. | |
| 9,124,955 B2 | 9/2015 | Geva et al. | |
| 9,233,244 B2 | 1/2016 | Pal et al. | |
| 9,539,944 B2* | 1/2017 | Tzirkel-Hancock | B60Q 9/00 |
| 2012/0116198 A1* | 5/2012 | Veen | A61B 5/04284 600/372 |
| 2012/0259181 A1 | 10/2012 | Fujita et al. | |
| 2012/0330173 A1 | 12/2012 | Park et al. | |
| 2013/0325202 A1* | 12/2013 | Howard | B60W 30/08 701/1 |
| 2015/0032382 A1* | 1/2015 | Lee | A61B 5/18 702/19 |

(Continued)

FOREIGN PATENT DOCUMENTS

| | | |
|---|---|---|
| CN | 204147427 U | 2/2015 |
| EP | 2308559 A2 | 4/2011 |

*Primary Examiner* — Hoi C Lau

(74) *Attorney, Agent, or Firm* — Brooks Kushman P.C.

(57) ABSTRACT

A vehicle seating system is described that can detect and optionally quantify a drowsiness state and/or and emotional state of a seat occupant in the vehicle. A seat is mounted in a vehicle and houses a wireless electromagnetic sensing system at least partially integrated into the seat. These sensed signals can be used to determine the occupant's state. When the state exceeds a threshold, then wireless stimulation emitters output a stimulation signal to the occupant to alter the emotion state or drowsiness state to move the occupant to below the threshold and to a calm state or an alert state. The system can also use additional physiological sensor to measure at least one of a heart rate, a respiration rate, or both of the occupant to be used with the electromagnetic sensing at the seat.

19 Claims, 3 Drawing Sheets

(56) References Cited

U.S. PATENT DOCUMENTS

| | | | |
|---|---|---|---|
| 2015/0328985 A1* | 11/2015 | Kim | H04N 5/23229 |
| | | | 180/272 |
| 2015/0360608 A1* | 12/2015 | Tzirkel-Hancock | B60Q 9/00 |
| | | | 297/217.1 |
| 2016/0133151 A1* | 5/2016 | O'Dowd | G06F 3/011 |
| | | | 434/236 |
| 2016/0260343 A1* | 9/2016 | Resl | A61B 5/02405 |
| 2016/0292988 A1* | 10/2016 | McCleary | G08B 21/14 |
| 2017/0068245 A1* | 3/2017 | Scofield | G08G 1/0112 |
| 2017/0136842 A1* | 5/2017 | Anderson | B60G 17/016 |
| 2017/0196497 A1* | 7/2017 | Ray | A61B 5/4094 |
| 2017/0355377 A1* | 12/2017 | Vijaya Kumar | B60W 40/08 |
| 2017/0367635 A1* | 12/2017 | Hur | A61B 5/0261 |
| 2018/0136191 A1* | 5/2018 | Asvadi | A61B 5/0077 |
| 2018/0143006 A1* | 5/2018 | White | G01V 8/10 |
| 2018/0189681 A1* | 7/2018 | Harrivel | A63F 13/42 |
| 2018/0197636 A1* | 7/2018 | Firminger | G16H 50/20 |
| 2018/0229674 A1* | 8/2018 | Heinrich | B60R 16/0231 |

* cited by examiner

SEATING SYSTEM WITH OCCUPANT STIMULATION AND SENSING

TECHNICAL FIELD

The present disclosure relates to seating systems with integrated stimulation to provide stimulation to seat occupant lessen drowsiness or counteract the emotional state, and, more specifically, to electromagnetic stimulation of the seat occupant via transcutaneous nerve stimulation.

BACKGROUND

Distracted or drowsy driving of a motor vehicle, which is a type of driver error, is a significant cause of preventable road accidents. Vehicle systems that assist in warning a driver of distracted driving or take action in such an occurrence may reduce the number of such accidents or attempt to mitigate damage caused by distracted or drowsy driving.

SUMMARY

An aspect of the present disclosure is a vehicle a system to stimulate a vehicle occupant to correct for an undesired emotional state or a drowsiness state, or both. Contactless sensing and stimulation of the vehicle occupant can be used to allow freedom of movement of the occupant. The system can include a contactless electro-dermal potential sensing system integrated into a vehicle cabin to sense a vehicle occupant and configured to output an electro-dermal potential signal, and a controller to receive the electro-dermal potential signal from the electro-dermal potential sensing system to determine an emotional state, a drowsiness state, or both of the vehicle occupant using the electro-dermal potential signal and, if a determined state of the vehicle occupant passes a threshold, outputting a stimulation signal. A contactless stimulation emitter system is in the vehicle seat supporting the vehicle occupant to output wirelessly a stimulation signal to the vehicle occupant to change the emotion state, a drowsiness state, or both of the vehicle occupant.

In an aspect, the controller receives additional vehicle occupant-related data from at least one additional vehicle sensor and outputs the stimulation signal using both the electro-dermal potential signal and the vehicle occupant-related data.

In an aspect, the vehicle occupant-related data includes a video from an imager in the vehicle cabin, heart rate data from seat sensors or steering wheel sensors.

In an aspect, the vehicle includes a seat configured to support the person as the occupant and to be mounted in the vehicle cabin. The electro-dermal potential sensing system can include a contactless sensor mounted in the seat adjacent a head or neck of the occupant. The contactless stimulation emitters of the stimulation system can be mounted in the seat adjacent a head or neck of the occupant.

In an aspect, the electro-dermal potential system includes a plurality of contactless sensors mounted in the seat; and wherein the seat includes a head restraint, and wherein the plurality of contactless sensors includes one or more head restraint sensors mounted in the headrest to measure electro-dermal potential at a head or neck of a seat occupant.

In an aspect, the contactless stimulation emitter includes a plurality of contactless emitters; and wherein the seat includes a head restraint, and wherein the plurality of contactless emitters includes one or more head restraint emitters mounted in the headrest to stimulate at least one of a sympathetic system, a parasympathetic system, or both at a head or neck of a seat occupant.

In an aspect, the seat includes a driver warning device to indicate to the driver that the threshold of the emotional state or drowsiness state of the occupant is exceeded.

In an aspect, the controller measures emotional state based on individual frequency components in the electro-dermal potential signal.

In an aspect, the controller uses the electro-dermal potential signal to determine the drowsiness state or emotional state of the occupant and when a threshold for either the drowsiness state or emotional state is detected outputs a further control signal to increase a time to impact variable in an object avoidance calculation.

In an aspect, the controller, before outputting the stimulation signal outputs an occupant alert on at least one of a visual display or an audio output to inform the occupant of the stimulation signal from the contactless stimulation emitter to at least one of a sympathetic system, a parasympathetic system, or both at a head or neck of a seat occupant.

In an aspect, the controller, before outputting the stimulation signal, receives a manual input from the occupant via voice, hand controls etc. (HMI) to output a stimulation signal from the contactless stimulation emitter to at least one of a sympathetic system, a parasympathetic system, or both at a head or neck of a seat occupant.

In an aspect, the controller, before outputting the stimulation signal outputs an occupant alert on at least one of a visual display or an audio output to request permission from the occupant to initiate the stimulation signal from the contactless stimulation emitter to at least one of a sympathetic system, a parasympathetic system, or both at a head or neck of a seat occupant.

In an aspect, the controller, before outputting the stimulation signal receives a trigger from a machine learning system or AI system that learns the usage pattern and cross-reference it with data such as vehicle speed, GPS positioning, occupant position in the vehicle, etc. to initiate the stimulation signal from the contactless stimulation emitter to at least one of a sympathetic system, a parasympathetic system, or both at a head or neck of a seat occupant. The machine learning system or AI system can be positioned in a vehicle and can determine when a stimulation signal is appropriate and can trigger the stimulation system.

In an aspect, a navigational position signal from a navigational position sensor to detect position of a vehicle, and wherein the controller uses the navigational position signal and the electro-dermal potential signal to determine a likelihood of the occupant being in either a drowsiness state or an emotional state.

In an aspect, a vehicle system can include a sensing system to sense an occupant state. The sensing system can be integrated into the vehicle or a vehicle cabin to sense a vehicle occupant and configured to output a sensed signal. The sensed signal can indicate an emotional state or alter state of the occupant, e.g., the vehicle driver. A controller is configured to receive the sensed signal from the sensing system to determine a state of the vehicle occupant including at least one of an emotional state, a drowsiness state, or both using the sensed signal. The controller can load from a memory a baseline state, e.g., a threshold value or a range, of the occupant's state. The controller can compare the determined state to the baseline occupant state. With the determined state being outside the baseline, the controller outputs a stimulation signal. A contactless stimulation emitter is mounted in the vehicle adjacent the occupant, e.g., in a vehicle seat supporting the vehicle occupant. The emitter is configured to output wirelessly a stimulation signal, upon receipt of the stimulation signal from the controller, to the vehicle occupant to change the state of the vehicle occupant.

In an aspect, the contactless stimulation emitter includes a transcutaneous nerve stimulator.

In an aspect, the controller outputs an occupant notification into the vehicle cabin indicating that the determined state exceeds the baseline occupant state and requests an input from the occupant to allow outputting the stimulation signal to the emitter.

In an aspect, the controller can receive an indication from the occupant to trigger the stimulation signal without waiting for the determination that the determined state is outside the baseline.

In an aspect, the controller can trigger secondary state altering treatment to return the determined state to within the baseline.

In an aspect, the secondary state altering treatment includes at least one playing an audio message through a speaker in the vehicle cabin, playing a preselected song through the speaker in the vehicle cabin, displaying a preselected image on a video display in the cabin.

In an aspect, the occupant can manually trigger the emission from the emitters by inputting through HMI in the vehicle to the controller to trigger the output signal. The sensors, controller operation, and the emitter are only operable to trigger emission of a transcutaneous signal to alter an occupant state when the occupant manually activates the sensors, the controller, and the emitter.

In an aspect, the emitter is configured to emit an electromagnetic field to stimulate at least one of a cranial nerve, a paravertebral nerve or both to stimulate a parasympathetic system, a sympathetic system, or both, of the occupant.

Any of the above examples may be combined with each other to form additional embodiments of the present disclosure. Other embodiments of the present disclosure will be apparent from the remainder of the present disclosure.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The present systems include a contactless electrical stimulation system embedded in the head rest or seat back with emitter electrodes in the close proximity to the occupant's head, neck and spine. The emitter electrodes can be contactless, e.g., under the outer layer of a seat, without direct contact to the occupant's skin. The stimulation system, by appropriate contactless stimulation with the emitter electrodes, stimulate the occupant's nerves to induce a return to a neutral baseline. In an aspect, the stimulation is transcutaneous nerve stimulation of the occupant. For example, if the occupant is determined to be drowsy, then an awakening signal is emitted from the emitter electrodes to the occupant. If the occupant is determined to be stressed, then an calming signal is emitted from the emitter electrodes to the occupant.

The vehicle seating system can include sensors to sense motion sickness onset of experience by a driver or occupant of the vehicle who may be seated in a vehicle seat. The seat may be configured to support an occupant and be mounted in a vehicle. Various sensors may be used to detect physiological parameters that indicate motion sickness. When motion sickness is detected, then the system can emit a stimulation electromagnetic signal from the emitters.

The present system can include one or more electro-dermal potential, contactless sensors at least partially integrated into the seat to sense electro-dermal potential signals of the occupant and configured to output an electro-dermal potential signal for stimulation of the occupant. The controller is positioned in the vehicle to receive the sensed electro-dermal potential signal(s) and sensed physiological parameters of the occupant to determine a state of the occupant in need of stimulation. The occupant states that may require stimulation include motion sickness, drowsiness, emotional stress, and the like. The stimulation signal can stimulate the nerves to induces a return to a neutral baseline A neutral baseline can include an awake sensation in the case of occupant drowsiness or, alternatively, a state of calm whenever the occupant is in a state of stress.

Figure 1:
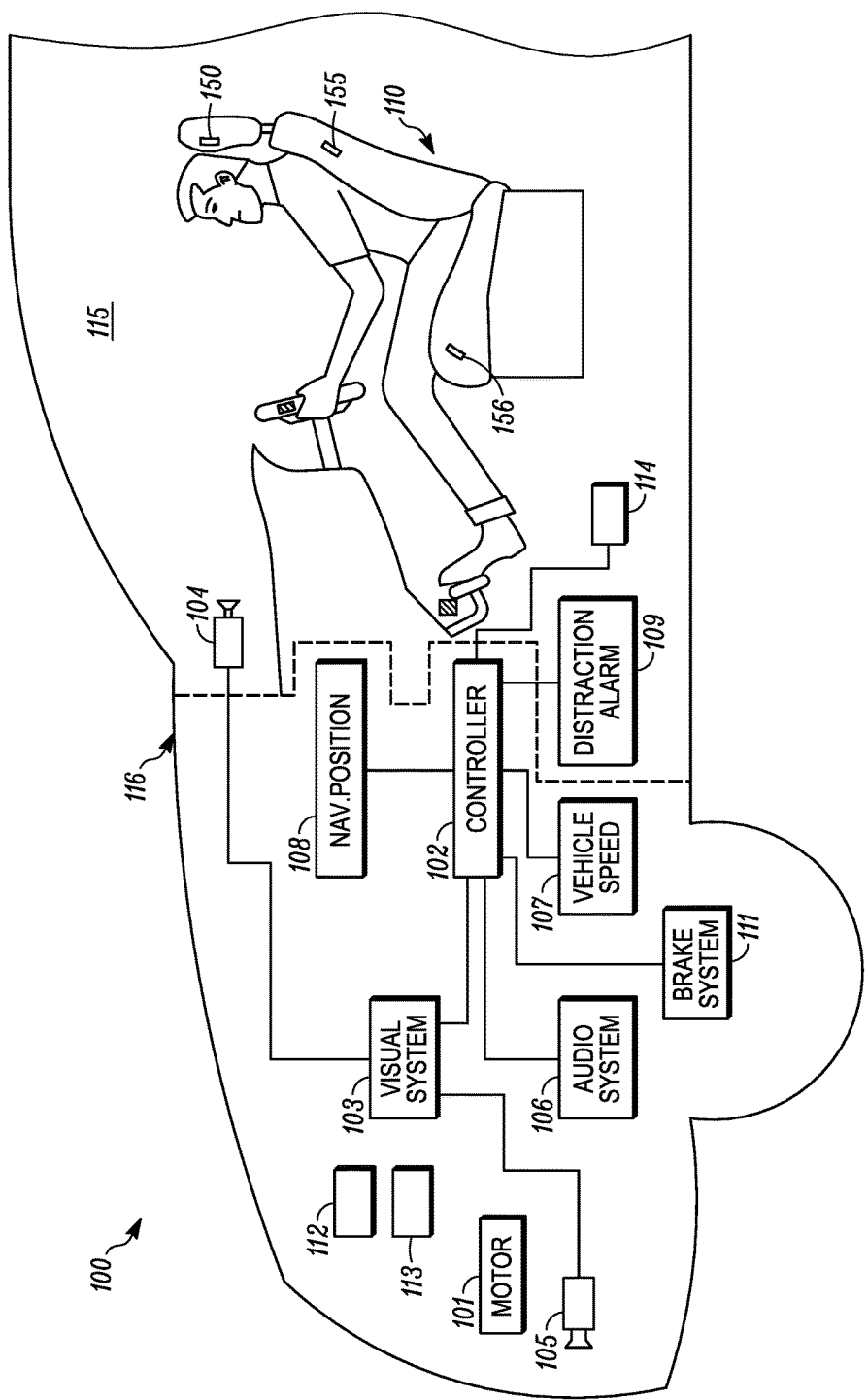
FIG. 1 is a schematic view of a vehicle according to an example embodiment.

FIG. 1 shows a vehicle 100 including a cabin 115 and an engine bay 116, which can be forward of the cabin 115. The engine bay 116 houses a motor 101 that provides motive power to the vehicle. A controller 102 includes an electrical signal processor adapted to execute instructions, which can be stored in a memory. The instructions can process sensed signals according to rules loaded into the controller 102. The sensed data can be stored in memory associated with the controller 102. The sensed data stored in memory associated with the controller 102 can be analyzed to determine patterns by a machine learning system and/or AI system. The instructions can also produce output signals to cause emitters to emit stimulation signals to an occupant, e.g., using transcutaneous nerve stimulation. These stimulation signals can counter the drowsiness state, the distracted state or the stressed state of the occupant. The stimulation signals are intended to have a cognitive effect on the occupant to which the stimulation signals are applied.

Visual systems 103 are provided to receive instructions from the controller 102 and produce visual displays in the vehicle, e.g., in the cabin on display screens, the dashboard, a mobile electronic device associated with the vehicle. The displays produced by the visual systems can be images sensed by and internal pointing camera 104, an external pointing camera 105, collision warnings, distraction warnings and the like. The visual system 103 can process the image data from the cameras 104, 105 before providing the image data to the controller 102. The camera 104 is directed to sense images in the vehicle cabin 115. The camera 105 is mounted in the vehicle and directed to sense images outside the vehicle. The visual system 103 can process in images to identify objects and the position of the driver in an example embodiment. This data can be provided to the controller 102.

An audio system 106 can be part of a head unit in the vehicle. The audio system 106 can sense audio in the cabin 115 and output audio into the cabin, e.g., using multiple speakers 114. The audio output from the audio system 106 can be warnings as described herein based on instruction from the controller 102. The audio warnings can be spoken words or tones to indicate driver distraction, change in settings, imminent danger, activation of collision warning system or combinations thereof.

A vehicle speed sensor 107 is provided to detect the speed of the vehicle and provide a speed signal to the controller 102.

A navigational position system 108 detects the position of the vehicle by receipt of satellite signals or ground based position signals. The navigational position system 108 can include a global navigation satellite system (GNSS) such as Global Positioning System (GPS), Beidou, COMPASS, Galileo, GLONASS, Indian Regional Navigational Satellite System (IRNSS), or QZSS. The navigational system can include a receiver that receives differential correction signals in North American from the FAA's WAAS system. The navigational position system 108 provides accurate position of the vehicle to the controller 102.

An alarm 109 is positioned in the cabin. The alarm 109 can include mechanical alarms like vibration devices that can be positioned in the steering wheel or the seat. The distraction alarm 109 can be a signal to vibrate a mobile electronic device associated with the vehicle and a passenger in the vehicle.

A vehicle seat 110 is positioned in the cabin 115 and is configured to support a person, e.g., a driver or a passenger. The seat 110 includes a plurality of sensors 150, 155, 156 to detect various biometric characteristics of the person. The sensors 150 can be contactless and can sense EDP adjacent the head or neck of the seated person. The sensors 155 and 156 can detect other biometric information. The sensors 155, 156 can sense the heart rate of the occupant of the seat in an example embodiment. The sensors 155, 156 can sense the breath rate of the occupant of the seat in an example embodiment. The sensed EDP data from the sensors 150 can be combined with either or both of the sensed hear rate and sensed breath rate from the sensors 155, 156 to detect and quantify drowsiness of the occupant, particularly, the driver, in the seat 110. The seat 110 includes a plurality of emitters 160 to emit electromagnetic signals from the seat to the occupant. The emitters 160 can be contactless and can emit a wireless stimulation signal to the occupant. The emitters act as stimulation electrodes and can include electromagnetic antennas capable of generating an electromagnetic field of variable amplitude and frequency. The electromagnetic field is capable of stimulating the cranial or paravertebral nerves which in turn cause the stimulation of the parasympathetic or sympathetic system of the occupant. The use of the electromagnetic field allows the stimulation emitters to be contactless, which allows the occupant to have freedom of movement in the vehicle that an occupant is accustomed, e.g., changing posture in the seat, egress from the vehicle and the like.

The sensors 150, 155, 156 and the stimulation emitters 160 are positioned in the single seat in an aspect of the present disclosure. This results in the individualization of the sensing and stimulation to the seat occupant. Other occupants may have their own sensing and stimulation. This results in only a single occupant that is need of stimulation based on drowsiness state or emotional state receiving stimulation. Also, the use of stimulation emitters that emit an electromagnetic signal to only the occupant, results in only the occupant being notified of the occupant's state. When the vehicle produces an audible warning, a visual warning, seat vibration, a climate control change, or the like, the entire vehicle cabin is notified of the issue with the occupant. In some instances, the notification to the entire vehicle cabin may not be desired.

The stimulation emitters 160, in an aspect of the present disclosure, are adapted to emit signals to stimulate neurons and other cell types in connected networks that process sensory input, or control behavioral and cognitive functions. Neurons communicate primarily through electrochemical pulses that transmit signals between connected cells to, within, and between brain areas. The stimulation signals are intended to affect electric fields and electrochemical signaling in neurons to modulate the pattern of neural activity and cause altered cognitive states. Electrical stimulation applied to the head and neck area from the emitters 160. This can be done through transcranial electric stimulation (TES) to affect endogenous brain rhythms.

A brake system 111 is provided to brake the wheels of the vehicle. The brake system 111 can be activated by the driver and can also be activated automatically by the controller, e.g., when a drowsy state or distracted driving due to an emotional state is detected, a crash is detected as imminent or an imminent danger is detected.

A laser sensing system 112, e.g., a LIDAR, is provided. The laser sensing system 112 emits light in pulses and detects the light returned after the light reflects of object external to the vehicle 100. The laser sensing system 112 can produce a digital three-dimensional representation of the external environment around the vehicle in the direction of the light pulses. The laser sensing system 112 can perform laser scanning to produce a representation around the vehicle. The external environment can include other vehicles, signs, and other objects. The representation or individually identified objects can be provided to the controller 102 for use in the vehicle as described herein.

A RADAR sensing system 113 is provided in the vehicle. The RADAR sensing system 113 emits radio frequency energy pulses and detects the returned pulses to identify objects around the vehicle or map the external environment. The representation or individually identified objects can be provided to the controller 102 for use in the vehicle as described herein.

Other typical vehicle systems may be included in the vehicle 100 but are not illustrated for clarity of the drawings. The controller 102 may provide inputs to these other systems.

Figure 2:
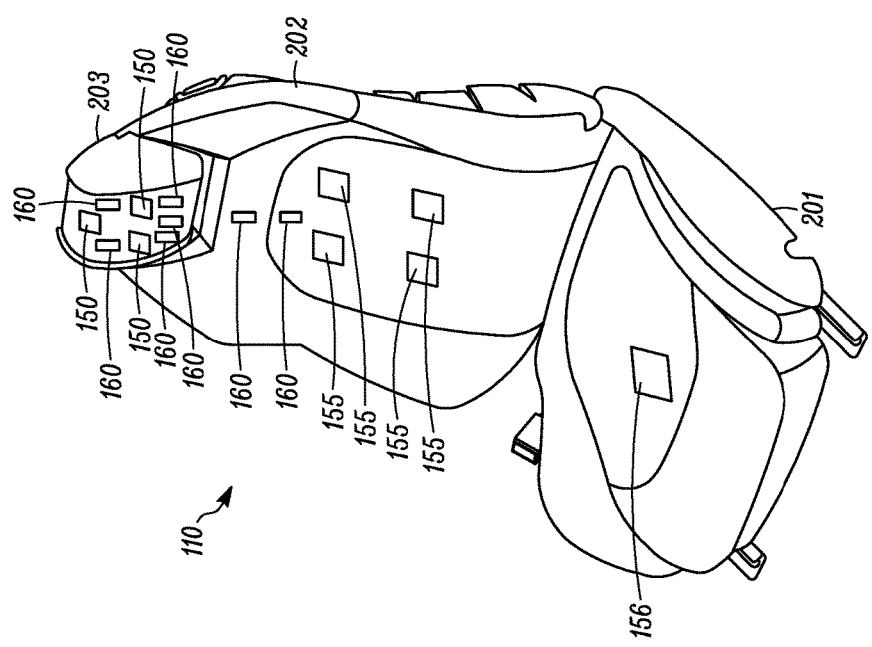
FIG. 2 is a schematic view of a vehicle seat with stimulators therein according to an example embodiment.

FIG. 2 shows the vehicle seat 110 configured to be fixed in a cabin of a motor vehicle. The seat 110 is adapted to support a person on a base 201 in an upright position against a seat back 202. The base 201 is fixed to the floors in the vehicle cabin, e.g., by slidable rails. A headrestraint 203 may be positioned at the top of the seat back. Each of the base 201, seat back 202, and headrestraint 203 include a rigid frame, comfort layers on the frame and an external covering. A plurality of sensors 150, 155, 156 can be supported in the seat. A plurality of first sensors 150 may be positioned in the headrestraint 203 and adapted to sense EDP signals from the occupant of the seat. A plurality of second sensors 155 may be positioned in the seat back 202. The plurality of second sensors 155 may also sense EDP signals from the occupant. The plurality of second sensors 155 may include at least one sensor that does not sense EDP signals. One or more third sensors 156 are positioned in the seat base 201. The third sensors 156 may also sense EDP signals. The plurality of second sensors 155 may include at least one sensor that does not sense EDP signals and may, e.g., sense presence of a person in the seat and sense weight of the occupant of the seat. The sensors 150 to develop raw EDP signals, which are filtered the raw signals to produce analysis signals including frequency components relevant to EDP of the person in the seat while attenuating unrelated frequency components.

The drowsiness state or the anger/irritation state of a person is monitored using the EDP at the head, neck or torso of the occupant of the seat 110 by the sensors 150 in conjunction with the sensors 155, 156. The sensors 150 are positioned proximate to portions of the skin adjacent the head to develop raw EDP signals. The EDP raw signals can be filtered to produce at least one bandpass-filtered drowsiness or anger/irritation state-indicating EDP signal representative of raw EDP signal magnitude within a predetermined frequency range as an indication of the emotional or physical state of the seated person.

The controller 102 uses the sensed signals from the seat or other sensors in the vehicle cabin to determine the state of the occupant. Based on the determined state, the controller 102 can output an occupant stimulation signal from the stimulation emitters 160 to attempt to return the occupant to a normal state, e.g., below a drowsiness or irritation/anger threshold.

Figure 3:
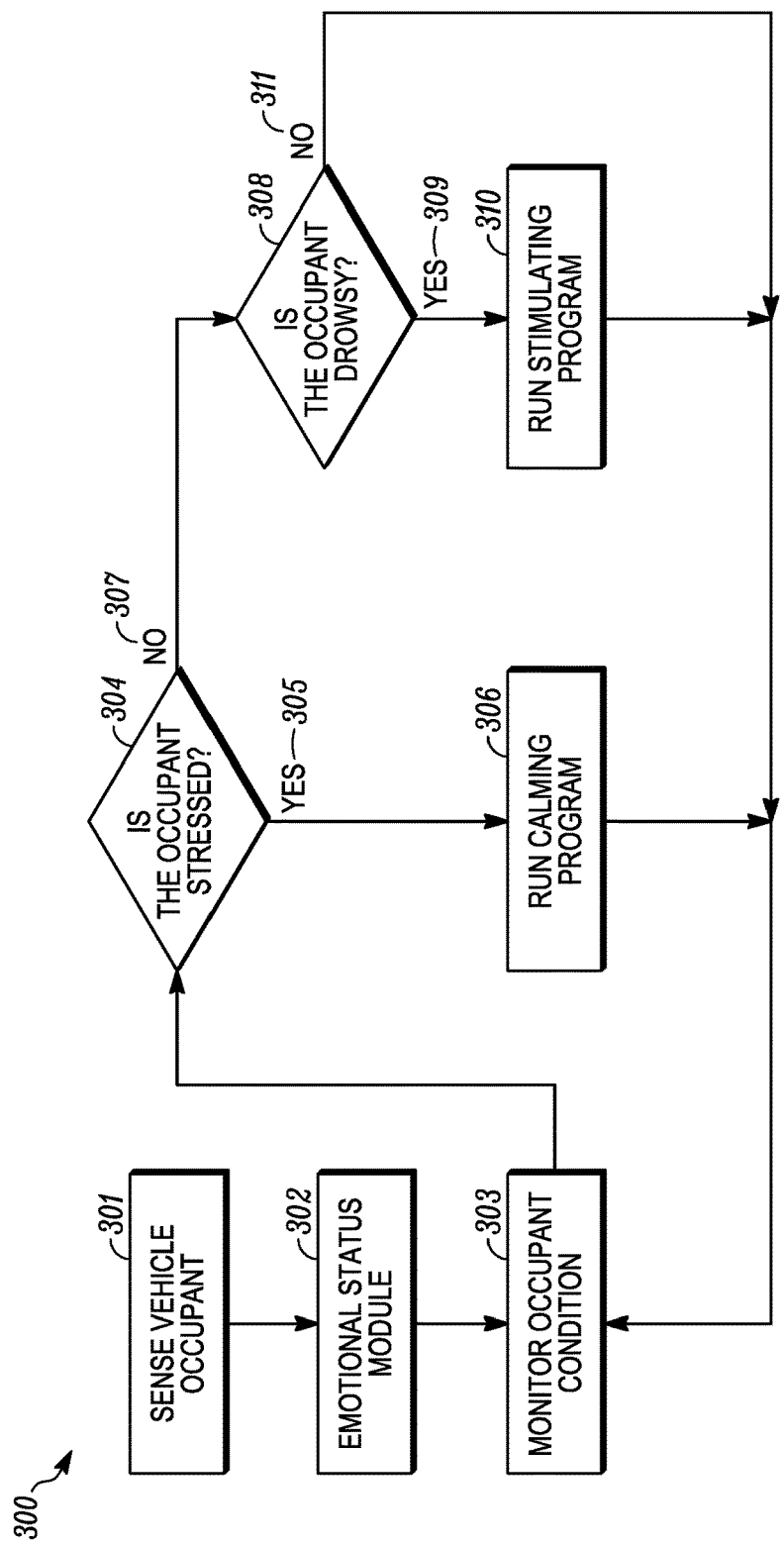
FIG. 3 is a functional block diagram of a vehicle system according to an example embodiment.

FIG. 3 shows process 300 that can be implemented in the vehicle 100 to sense an emotional state or a physical state of the occupant of the seat and provide a contactless stimulation signal to return the occupant to a normal state. The process 300 can be implemented in the vehicle 100 in an example embodiment. At 301, the process starts by monitoring the occupant of a vehicle seat (e.g., a driver). The monitoring starts by sensing the presence of the occupant in the seat. The occupant can opt-in to the anti-stress and anti-drowsiness systems in the vehicle. The monitoring can include sensing the EDP of the occupant, e.g., using contactless sensors in the seat, and a secondary physiological parameter of the driver. The EDP can by sensed, at least in part, about the head of the occupant. The secondary physiological parameter can be heart rate or respiration rate.

At 302, an emotional state module can load the baseline signals that indicate the emotion state of the occupant. These can be sympathetic and parasympathetic signals of the occupant in an alert state and a calm state. Both the EDP and the secondary physiological parameter are used to determine the emotional status of the vehicle occupant. These baseline values can be loaded into the controller 102.

At 303, the occupant is contactlessly monitored. The EDP is sensed which can include brain waves that indicate drowsiness, an irritation state or an anger state of the occupant. The secondary physiological parameter(s) can also indicate a drowsy state and can include, e.g., deep regular respiration, slowing respiration, slowing heart rate and the like. The secondary physiological parameter(s) can also indicate an anger state or an irritated state can include, e.g., heart rate, facial expression, flushness of skin tone, body temperature, grip pressure on the steering wheel, and the like. These secondary parameters can be monitored in the vehicle cabin and used as inputs to determine the drowsiness state, the anger state or the irritation state.

At 304, it is determined if the occupant is in a stressed state, e.g., in an anger state or irritation state. If yes, the process moves to step 305 and then step 306 to run a calming operation by the system. The controller can activate a calming program to activate the stimulation emitters to output an electromagnetic signal to induce a calming effect on the occupant. The stimulation emitters wirelessly output a stimulation signal that interacts with at least one of the occupant's sympathetic and parasympathetic systems to return the occupant to a calm state, i.e., move from a state of anger or irritation to a state of calm. The process then continues to monitor the occupant at 303. If the occupant is not stressed, then then the process moves to step 307 and then to step 308.

In an aspect, the determination that the occupant is in a stressed state at 304 can also be triggered by the occupant. The occupant may sense that he/she is stressed and input into the controller through a human-to-machine interface that the occupant is stressed. The controller can then trigger the calming program at 306.

At 308, it is determined if the occupant is in a drowsy state, If yes, the process moves to step 309 and then step 310 to run a stimulation operation by the system. The controller can activate a stimulation program to activate the stimulation emitters to output an electromagnetic signal to induce a stimulation effect on the occupant. The stimulation emitters wirelessly output a stimulation signal that interacts with at least one of the occupant's sympathetic and parasympathetic systems to return the occupant to an alert state. The process then continues to monitor the occupant at 303. If drowsiness is not determined, then the process moves to 311 and continues to monitor the occupant at 303.

In an aspect, the determination that the occupant is in a drowsy state at 308 can also be triggered by the occupant. The occupant may sense that he/she is drowsy and input into the controller through a human-to-machine interface that the occupant is drowsy. The controller can then trigger the stimulating program, anti-drowsy, program at 310.

The stimulation of the occupant as used herein uses stimulation emitter to wirelessly output an electromagnetic stimulation signal to the occupant. Other indicators of the state of the occupant can also be used. In an example, drowsiness and anger warnings can be output to the occupant through the vehicle systems, e.g., a visual indication on the dashboard display or in a heads-up display. The vehicle may provide an audio warning, e.g., a tone or a spoken voice to warn the occupant of their emotional state or drowsiness. Other forms of warnings may be used. The seat may be equipped with a vibration device that vibrates the seat with varying patterns of the vibration. The steering wheel may include a vibration device to vibrate the steering wheel when an undesired emotional state or drowsiness is detected as described herein.

The EDP signals can be separated into various sub-signals, e.g., at different frequencies, by using filters to allow certain divisions into sub-bands. These sub-bands may overlap in frequency ranges. A first sub-signal can be up to four hertz. A second sub-signal can be four hertz to seven hertz. A third sub-signal can be seven hertz to fourteen hertz. A fourth sub-signal can be fourteen hertz to about thirty hertz. A fifth sub-signal can be about thirty hertz to about one hundred hertz. Other sub-signals may overlap these ranges for the first through sixth sub-signals, e.g., from eight hertz to thirteen hertz. The relationships between these sub-signals can be used to determine whether the emotional state of occupant or whether the occupant is drowsy. The patterns of the sub-signals or the ratios of multiple sub-signals to each other can be used to determine if a driver is drowsy, angry or irritated.

Historical long term data related to detected emotional state or drowsiness state can be processed secondary to the real-time algorithms to provide a variety of statistical information for both the occupant and machine learning systems. The long term data may be stored in the vehicle or off-vehicle. The vehicle may include electronic communication to an external server, e.g., over WiFi, mobile communication networks, such as cellular communications, and the like. The long term emotional state calculations may be used to alter the instructions for determining the emotional state, for mitigating false positives, and for determining the emotional state baseline. The vehicle can use the emotional state and drowsiness state status of the driver to manipulate reaction times of various vehicle safety systems, e.g., the adaptive braking system, to optimize the response of the system itself. This may reduce the risk of forward collisions.

The present disclosure is generally directed to seat stimulators and optional seat sensors both of which can be embedded in any part of the foam, trim, frame, headrest or a combination thereof of a vehicle seat. The stimulators can operate to emit an electromagnetic signal to contactlessly stimulate the cranial or paravertebral nerves of the seat occupant, which in turn cause the stimulation of the occupant's parasympathetic or sympathetic system. The sympathetic and parasympathetic systems are responsible of opposite effects on the body with the former responsible for the "fight or flight" response and the latter responsible for the "rest and digest" response. The stimulation signal output by the stimulators is designed to match the normal, non-stressed, calm state of the vehicle occupant.

Turning to the sensors, at least one of the sensors uses non-surface detection at a distance to determine the electro-dermal potential (EDP) originating primarily from cortical activity. This will reveal high-level central nervous system (CNS) functions such as anger, agitation, drowsiness or distraction. The systems described herein employ real-time processing of the electrical potential fluctuations, e.g., comparing various frequency bands of the sensed signal with respect to each other. These can act as the primary brain activity quantitative classifiers. The present systems may use the sensed signals along with other sensor information to determine false positives of drowsiness based on the sensed EDP signal. This system, through the acquisition of the appropriate physiological metrics, and use of a software algorithm, is capable of determining if the occupant is distracted or drowsy and not attentive to the road task of the moment while correcting for false positive indications of drowsiness. Upon determination that the occupant is drowsy or distracted, the system can emit a stimulate the occupant through the emitters, which are not in direct mechanical contact with the occupant.

A contactless EDP sensing system can be integrated with the seat including one or more sensors embedded in any part of the seat, e.g., the foam, the trim, the headrest or a combination thereof. The contactless EDP sensing system can acquire of the appropriate physiological metrics (heart rate, HRV, breathing rate, EDP pattern shift and the like.) of the seat occupant, e.g., the driver. A controller can receive the sensed physiological metrics and determine if the occupant is drowsy and therefore if attention and reaction time is affected. The controller can be adapted to individual occupants using an automated user-specific calibration.

The contactless sensors can also be positioned in the steering wheel and can operate to sense the EDP of the driver at the driver's hands. The steering wheel sensors can also sense the pulse, to determine heart rate or heart rate variability, which can be used to determine the drowsiness or distraction of the driver.

This system, is also comprised of inward cameras, strategically positioned to look at the driver. Inward cameras are used in conjunction with the drowsiness detection system to achieve sensor fusion and increase specificity. The camera generates multiple images of the occupant, which can be analyzed to determine additional occupant metrics. The metrics can include head position, a blink rate, a head movement facial expression, and the like.

The use of various metrics from different sources provides an objective quantification of the occupant's state. The state quantification can be combined with other data in the vehicle to prevent false indications of occupant state. If the occupant's quantified state exceeds a state threshold, then the vehicle may automatically trigger stimulation to return the occupant to a more natural clam state outside the threshold.

The present system can be used in an autonomous vehicle or a semi-autonomous vehicle to keep the driver alert on the road and the actions of the vehicle.

Road rage-induced stress or a state of drowsiness are common while driving a vehicle. These states can result in longer reaction times and potentially more vehicle accidents. The embodiment described herein can be included as part of a wellness package, where a biometric system is capable to accurately detect the psycho-physiologic state of the occupant. Based on the occupant's status (i.e., stress/anger, or drowsiness), the examples described herein can deploy the treatment most appropriate to counteract the occupant's status and return the occupant's status to a neutral baseline.

While various embodiments described herein are described as sensing and stimulation by the vehicle, the occupant may also manually trigger the sympathetic/parasympathetic stimulation to counteract the occupant's status and return to a neutral baseline. The stimulation could be triggered by a switch, a voice command or an interaction with the vehicle HMI.

While the present vehicle is schematically illustrated as a passenger vehicle, the disclosure is not so limited. The vehicle for purposes of this disclosure include trucks, tractors, vans, boats, vessels, busses, trains, airplanes, mobile farm equipment, motorcycles, and the like. The drowsiness detection and quantification systems and methods described herein can be adapted to any of these vehicles, even beyond automotive and personal vehicles. In some embodiments, it is understood that the term "vehicle" or "vehicular" or other similar term as used herein is inclusive of motor vehicles in general such as passenger automobiles including sedans, sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

One example of electro-dermal potential may be electro-encephalograph (EEG), which is an electrophysiological monitoring method to record electrical activity of the brain. It is typically noninvasive, with the electrodes placed along the scalp, although invasive electrodes are sometimes used in specific applications. EEG measures voltage fluctuations resulting from ionic current within the neurons of the brain. In clinical contexts, EEG refers to the recording of the brain's spontaneous electrical activity over a period of time, as recorded from multiple electrodes placed on the scalp. Diagnostic applications generally focus on the spectral content of EEG, that is, the type of neural oscillations that can be observed in EEG signals.

The present disclosure is directed to a vehicle system that can detect drowsiness of an occupant in a vehicle seat. Drowsiness can be a feeling of being sleepy and lethargic or sleepiness, without actually falling asleep. In another example, sleeping is the extreme end of drowsiness. The examples used herein can quantify drowsiness up to sleeping. Drowsiness results in increased reactions time for a driver to respond to driving conditions. When the occupant is sleeping, then their drowsiness level would be 100%. In the case of sleeping, a vehicle with autonomous capabilities would take over the driving of the vehicle. Many of the embodiments herein are directed to detecting levels of drowsiness short of sleeping. This will allow the vehicle systems to activate drowsiness indicators or alarms to alter the driver of their current state. The vehicle systems can also alter the factors, e.g., time parameters and detection distances, to alert the driver to a potential hazard early that normal.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system, comprising:
    a contactless electro-dermal potential sensing system integrated into a vehicle cabin to sense a vehicle occupant and configured to output an electro-dermal potential signal;
    a controller to receive the electro-dermal potential signal from the electro-dermal potential sensing system to determine an emotional state, a drowsiness state, or both of the vehicle occupant using the electro-dermal potential signal and, if a determined state of the vehicle occupant passes a threshold, outputting a stimulation signal; and
    a contactless stimulation emitter in a vehicle seat supporting the vehicle occupant to output wirelessly a stimulation signal to the vehicle occupant to change the emotion state, a drowsiness state, or both of the vehicle occupant.

2. The system of claim 1, wherein the controller receives additional vehicle occupant-related data from at least one additional vehicle sensor and outputs the stimulation signal using both the electro-dermal potential signal and the vehicle occupant-related data.

3. The system of claim 1, wherein the vehicle occupant-related data includes a video from an imager in the vehicle cabin, heart rate data from seat sensors or steering wheel sensors.

4. The system of claim 1, further comprising a seat configured to support the person as the occupant and to be mounted in the vehicle cabin;
    wherein the electro-dermal potential sensing system includes a contactless sensor mounted in the seat adjacent a head or neck of the occupant; and
    wherein the contactless stimulation emitter is mounted in the seat adjacent a head or neck of the occupant.

5. The system of claim 4, wherein the electro-dermal potential system includes a plurality of contactless sensors mounted in the seat; and wherein the seat includes a head restraint, and wherein the plurality of contactless sensors includes one or more head restraint sensors mounted in the headrest to measure electro-dermal potential at a head or neck of a seat occupant.

6. The system of claim 4, wherein the contactless stimulation emitter includes a plurality of contactless emitters; and wherein the seat includes a head restraint, and wherein the plurality of contactless emitters includes one or more head restraint emitters mounted in the headrest to stimulate at least one of a sympathetic system, a parasympathetic system, or both at a head or neck of a seat occupant.

7. The system of claim 4, wherein the seat includes a driver warning device to indicate to the driver that the threshold of the emotional state or drowsiness state of the occupant is exceeded.

8. The system of claim 1, wherein the controller measures emotional state based on individual frequency components in the electro-dermal potential signal.

9. The system of claim 1, wherein the controller uses the electro-dermal potential signal to determine the drowsiness state or emotional state of the occupant and when a threshold for either the drowsiness state or emotional state is detected outputs a further control signal to increase a time to impact variable in an object avoidance calculation.

10. The system of claim 1, wherein the controller, before outputting the stimulation signal outputs an occupant alert on at least one of a visual display or an audio output to inform the occupant of the stimulation signal from the contactless stimulation emitter to at least one of a sympathetic system, a parasympathetic system, or both at a head or neck of a seat occupant.

11. The system of claim 10, wherein the controller, before outputting the stimulation signal outputs a request on at least one of a visual display or an audio output to ask the occupant to initiate the stimulation signal from the contactless stimulation emitter to at least one of a sympathetic system, a parasympathetic system, or both at a head or neck of a seat occupant.

12. The system of claim 1, further comprising a navigational position signal from a navigational position sensor to detect position of a vehicle, and wherein the controller uses the navigational position signal and the electro-dermal potential signal to determine a likelihood of the occupant being in either a drowsiness state or an emotional state.

13. A vehicle system, comprising:
    a sensing system integrated into a vehicle cabin to sense a vehicle occupant and configured to output a sensed signal;
    a controller to receive the sensed signal from the sensing system to determine a state of the vehicle occupant including at least one of an emotional state, a drowsiness state, or both using the sensed signal, compare the determined state to a baseline occupant state stored in the vehicle system, and with the determined state being outside the baseline outputting a stimulation signal; and
    a contactless stimulation emitter in a vehicle seat supporting the vehicle occupant to output wirelessly a stimulation signal, upon receipt of the stimulation signal, to the vehicle occupant to change the state of the vehicle occupant, wherein the contactless stimulation emitter includes a transcutaneous nerve stimulator.

14. The vehicle system of claim 13, wherein the controller outputs an occupant notification into the vehicle cabin indicating that the determined state exceeds the baseline occupant state and requests an input from the occupant to allow outputting the stimulation signal to the emitter.

15. A vehicle system comprising,
    a sensing system integrated into a vehicle cabin to sense a vehicle occupant and configured to output a sensed signal;
    a controller to receive the sensed signal from the sensing system to determine a state of the vehicle occupant including at least one of an emotional state, a drowsiness state, or both using the sensed signal, compare the determined state to a baseline occupant state stored in the vehicle system, and with the determined state being outside the baseline outputting a stimulation signal; and a contactless stimulation emitter in a vehicle seat supporting the vehicle occupant to output wirelessly a stimulation signal, upon receipt of the stimulation signal, to the vehicle occupant to change the state of the vehicle occupant, wherein the controller can receive an indication from the occupant to trigger the stimulation signal without waiting for the determination that the determined state is outside the baseline.

16. The vehicle system of claim 13, wherein the controller can trigger secondary state altering treatment to return the determined state to within the baseline.

17. The vehicle system of claim 16, wherein the secondary state altering treatment includes at least one playing an audio message through a speaker in the vehicle cabin, playing a preselected song through the speaker in the vehicle cabin, displaying a preselected image on a video display in the cabin.

18. The vehicle system of claim 17, wherein the sensing system, controller operation, and the emitter are only operable to trigger emission of a transcutaneous signal to alter an occupant state when the occupant manually activates the sensing system, the controller, and the emitter.

19. A vehicle system comprising, a sensing system integrated into a vehicle cabin to sense a vehicle occupant and configured to output a sensed signal;

a controller to receive the sensed signal from the sensing system to determine a state of the vehicle occupant including at least one of an emotional state, a drowsiness state, or both using the sensed signal, compare the determined state to a baseline occupant state stored in the vehicle system, and with the determined state being outside the baseline outputting a stimulation signal; and a contactless stimulation emitter in a vehicle seat supporting the vehicle occupant to output wirelessly a stimulation signal, upon receipt of the stimulation signal, to the vehicle occupant to change the state of the vehicle occupant, wherein the emitter is configured to emit an electromagnetic field to stimulate at least one of a cranial nerve, a paravertebral nerve or both to stimulate a parasympathetic system, a sympathetic system, or both of the occupant.

* * * * *